United States Patent [19]
Arroyo

[11] Patent Number: 5,141,794
[45] Date of Patent: Aug. 25, 1992

[54] SUPERABSORBENT ARTICLE HAVING RELATIVELY THIN LIQUID ABSORBENT PORTION

[75] Inventor: Candido J. Arroyo, Lithonia, Ga.

[73] Assignee: AT&T Bell Laboratories, Murray Hill, N.J.

[21] Appl. No.: 431,510

[22] Filed: Nov. 3, 1989

Related U.S. Application Data

[60] Continuation-in-part of Ser. No. 378,956, Jul. 12, 1989, Pat. No. 5,082,719, which is a division of Ser. No. 115,123, Oct. 30, 1987, Pat. No. 4,867,526.

[51] Int. Cl.⁵ ............... A61F 13/15; A61L 15/16; B32B 5/14; B32B 5/26
[52] U.S. Cl. ................... 428/138; 428/218; 428/287; 428/296; 428/308.4; 428/311.5; 428/337; 428/340; 604/370; 604/372; 604/378
[58] Field of Search ........... 428/138, 218, 287, 308.4, 428/311.5, 337, 340; 604/370, 372, 378

[56] References Cited

U.S. PATENT DOCUMENTS

| | | |
|---|---|---|
| 3,653,382 | 4/1972 | Easley et al. . |
| 3,815,602 | 6/1974 | Johns et al. . |
| 3,889,679 | 6/1975 | Taylor . |
| 3,926,891 | 12/1975 | Gross et al. . |
| 3,949,130 | 4/1976 | Sabee et al. . |
| 3,973,063 | 8/1976 | Weber . |
| 3,980,663 | 9/1976 | Gross . |
| 3,987,792 | 10/1976 | Hernandez et al. . |
| 4,041,231 | 8/1977 | Gross . |
| 4,061,846 | 12/1977 | Gross et al. . |
| 4,070,218 | 1/1978 | Weber . |
| 4,077,410 | 3/1978 | Butterworth et al. . |
| 4,085,754 | 4/1978 | Ness et al. . |
| 4,150,943 | 4/1979 | Dehnert et al. . |
| 4,151,130 | 4/1979 | Adams . |
| 4,226,232 | 10/1980 | Spence . |
| 4,232,674 | 11/1980 | Melican . |
| 4,235,237 | 11/1980 | Mesek et al. . |
| 4,293,609 | 10/1981 | Erickson . |
| 4,306,559 | 12/1981 | Nishizawa et al. . |
| 4,500,315 | 2/1985 | Pieniak et al. . |
| 4,540,454 | 9/1985 | Pieniak et al. . |
| 4,573,988 | 3/1986 | Pieniak et al. . |
| 4,622,263 | 11/1986 | Ando et al. . |
| 4,657,538 | 4/1987 | Becker et al. . |
| 4,902,559 | 2/1990 | Eschwey et al. ............ 428/283 |

OTHER PUBLICATIONS

Article in Apr. 1988, p. 6 issue of "Nonwovens Industry".

*Primary Examiner*—James C. Cannon
*Attorney, Agent, or Firm*—E. W. Somers

[57] ABSTRACT

An article (20) which is adapted to be positioned adjacent, for example, to the body of an animal or of a human being is a layered structure which includes a liquid pervious layer (22) and a liquid impervious layer (26). The article is applied to cause the liquid pervious layer to be contiguous with the body of the animal or of the human being. Interposed between the liquid pervious and impervious layers is an absorbent core (24). The absorbent core includes at least one absorbent member (35) which comprises a relatively porous substrate portion (37) which has been impregnated with a superabsorbent material. Waste liquid given off by the animal of the human being passes through the liquid pervious layer and into the absorbent core. This causes the absorbent core to swell, absorbing the liquid uniformly and preventing pass-through of further liquid toward the outside as well as preventing flow back of the liquid into contact with the body.

14 Claims, 1 Drawing Sheet

SUPERABSORBENT ARTICLE HAVING RELATIVELY THIN LIQUID ABSORBENT PORTION

CROSS-REFERENCE TO RELATED APPLICATION

This application is a continuation-in-part application of application Ser. No. 07/378,956, now U.S. Pat. No. 5,082,719, which was filed on Jul. 12, 1989 as a divisional application of Ser. No. 07/115,123 which was filed on Oct. 30, 1987 and which issued as U.S. Pat. No. 4,867,526 on Sep. 19, 1989, both of said applications being commonly assigned herewith.

TECHNICAL FIELD

This application relates to a superabsorbent article having a relatively thin absorbent portion. More particularly, it relates to a disposable superabsorbent article such as, for example, a diaper having a relatively thin liquid absorbent core.

BACKGROUND OF THE INVENTION

Disposable superabsorbent articles, such as diapers, for example, have been popular for some time. Generally, such a product includes an absorbent core which is sandwiched between a liquid pervious layer and a liquid impervious layer.

One problem with disposable as well as with prior art cloth diapers is their inability to prevent rewetting. By rewetting is meant the recontacting of waste liquid which is contained in the absorbent core with the skin of an infant, for example. Because of the weight and the activity of the infant, a portion of the liquid is caused to flow from the absorbent core. The liquid penetrates the adjacent water pervious layer which is adjacent to the infant's skin and hence contacts the infant's skin. As should be apparent, this causes discomfort for the infant and may cause skin irritation, for example.

The foregoing problem has been overcome with a disposable diaper which comprises a water pervious layer, and a spongy, resilient and compressible, hydrophobic fibrous barrier layer. Also included is an absorbent core and a water impervious layer. Such a diaper is useful to minimize contact of waste liquid material in the absorbent core portion with the infant's skin and to provide a diaper having improved air circulation and an air cushion feel for the infant. Such a diaper is disclosed in U.S. Pat. No. 3,987,792 which also discloses that the diaper has improved strength in the area of the diaper pin or tab. Also, the physical form of retention capacity of the diaper following urination by an infant is excellent because of the resiliency of the diaper. When the infant urinates, the urine passes through the water pervious layer and fibrous layer into the absorbent core where it is absorbed. The weight of the infant tends to compress the barrier layer causing the fibers to become intermeshed. This reduces the void volume of the layer and forms a seal or barrier against re-entry of urine into the water pervious layer.

The problem with the just described diaper and others on the market is that, although it solves the rewetting problem, the addition of the barrier layer adds excessive bulk to the diaper. See also U.S. Pat. No. 4,077,410. As a result, the infant is encumbered with a bulky diaper which may cause fitting problems with respect to clothes.

What is needed and what seemingly does not appear in the prior art is a trim, relatively thin disposable superabsorbent article which may be used as a diaper, for example. The sought-after disposable superabsorbent article should be one which is effective to absorb body liquids such as waste liquid materials and which prevents rewetting.

SUMMARY OF THE INVENTION

The foregoing problems of the prior art have been solved by the superabsorbent article of this invention. A superabsorbent article of this invention includes a liquid pervious layer and a liquid impervious layer. Disposed between the water pervious layer and a liquid impervious layer is a liquid blocking layer which includes a substrate portion having a relatively high tensile strength and having a relatively high porosity. A superabsorbent material impregnates the substrate portion to fill substantially the cells thereof such that the substrate portion impregnated with the superabsorbent material has a relatively low porosity.

The substrate portion which preferably is non-woven and web-like is impregnated with a material which is held in the non-woven, web-like member in suspension without its being reacted. When exposed to water, the impregnating material reacts to swell and to prevent the passage of water therethrough. In a preferred embodiment, the impregnating material comprises a liquid swelling or so-called superabsorbent material. In another embodiment, substrate portion may be treated with a paste comprising a superabsorbent material. The impregnating material may be a polyacrylic acid having a saponification in a relatively wide range or it may be a polyacrylamide. Also, the impregnating material may comprise blends or salts of polyacrylic acid or polyacrylamide, or copolymers or derivatives of the acrylic acid and the acrylamide.

BRIEF DESCRIPTION OF THE DRAWING

Other objects and features of the present invention will be more readily understood from the following detailed description of specific embodiments thereof when read in conjunction with the accompanying drawings, in which.

DETAILED DESCRIPTION

Figure 1:
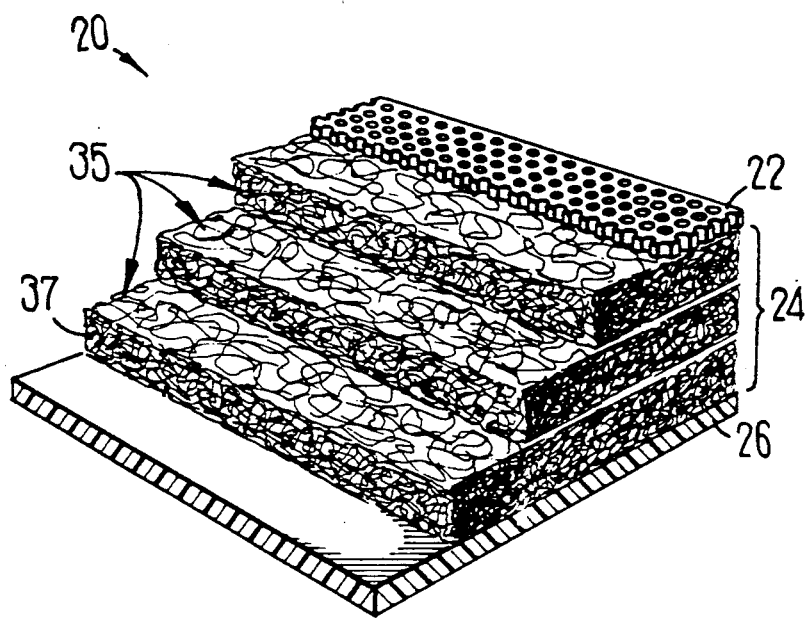
FIG. 1 is an exploded perspective view of a superabsorbent article which is constructed in accordance with the principles of this invention.
Figure 2:
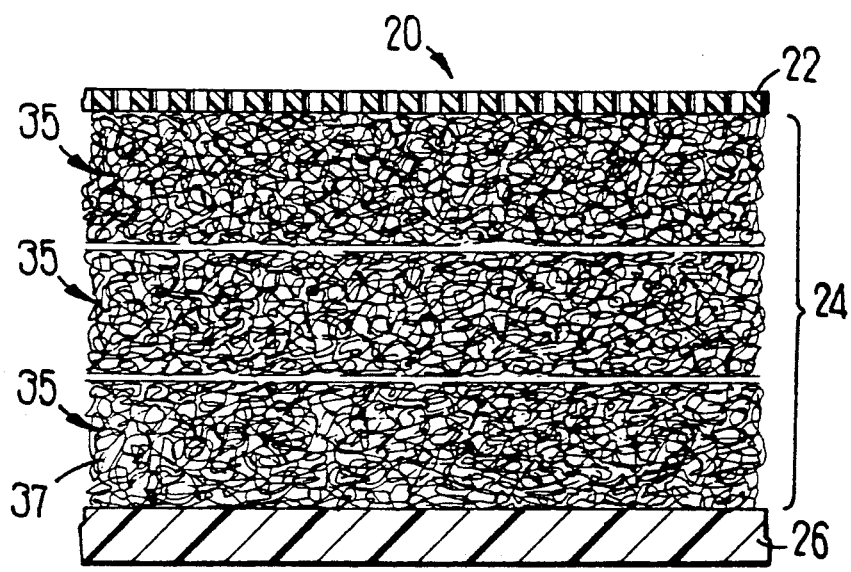
FIG. 2 is an end sectional view of the superabsorbent article of FIG. 1.

Referring now to FIGS. 1 and 2, there is shown a perspective view of a superabsorbent article in the form of a disposable diaper designated generally by the numeral 20. The diaper 20 includes a liquid pervious layer 22, an absorbent core 24 and a liquid impervious layer 26.

The liquid pervious layer 22 usually is provided in the form of a non-absorbent, soft, non-woven tissue which may have a large number of small perforations. This layer is readily water pervious and facilitates passage of waste liquid material toward an inner core portion of the diaper. The water pervious layer 22 is adjacent and, at least in part, contiguous the skin of a human being such as an infant or of an animal, when the infant, for example, is diaper-clad and should therefore have a softness and non-irritating nature which ensures the comfort of the infant. In general, the liquid pervious layer may be made of cellulose or of any of a wide variety of non-woven webs having the desired properties of softness to the sense of touch, often termed "hand" or "feel", porosity and hydrophobic action with respect to liquid material. Materials which are suitable for such use are well known in the art.

The layer 26 is made of a suitable waterproof non-absorbent, preferably resinous film-forming polymeric material which is liquid impervious such as, for example, a polyethylene film for preventing liquid from passing entirely through the superabsorbent article. Other suitable materials include, for example, polpropylene and polyvinyl chloride.

Disposed between the liquid pervious and impervious layers 22 and 26, respectively, is the absorbent core 24. The absorbent core 24 comprises at least one substrate or carrier portion 37 which is made of a hydrophobic material and which has been treated with a superabsorbent material. Advantageously, the treated substrate portion which is designated generally by the numeral 35 and which is referred to hereinafter as an absorbent member, is hydrophilic. A hydrophilic material is one that has a strong affinity for water in that it absorbs water easily. The superabsorbent article 20 which is shown in FIG. 1 preferably comprises a plurality of absorbent members 35—35, such as, for example, those which comprise the absorbent core 24.

In a preferred embodiment, the substrate portion 37 is a spunbonded non-woven polyester material and includes a web structure comprised of randomly-arranged fibers which are bonded primarily at the filament crossovers. Continuity of the fibers of the web, while not necessary to the invention, will provide the web with an increased tensile strength. The fibers may be formed of any plastic resin, or other appropriate material, which is substantially nonhygroscopic, and which has the capability of maintaining its shape. The fibers of the web structure are arranged so that air cells or pockets are formed.

A polyethylene terephthalate fiber product, formed into a web structure suitable for the substrate portion 37 as described above has been identified under the registered trademark "Reemay" by the E. I. du Pont de Nemours and Company, Incorporated of Wilmington, Del. Presently, the Reemay ® web structure is available in various thicknesses and densities from Reemay, Inc. of Old Hickory, Tenn. The properties of Reemay ® tapes are further defined and described in Bulletin R-1, dated March, 1986, entitled "Properties and Processing of Reemay ® Spunbonded Polyester" from E. I. du Pont de Nemours and Company, Incorporated, Wilmington, Del.

Although in a preferred embodiment, a spunbonded polyester substrate portion is used, others also are acceptable. For example, the substrate portion which is to be impregnated may be a nylon spunbonded fabric, polypropylene melt blown non-woven fabric, polyurethane spunbonded fabric or TCF cellulose fabric, for example.

Stiffness of the material for the substrate portion 37 is controlled by a combination of factors such as the number of fibers per unit volume, thickness of the material, size of the fibers and the amount and type of binder used in the material. Increasing the thickness of the material obviously increases the cost of the material per unit of surface area. Thus, at least three factors, formability of the substrate portion 37, cost of the substrate portion, and its liquid blocking capability must be considered and balanced in providing the proper material for a particular use.

In a preferred embodiment, the spunbonded polyester substrate portion 37 combines the thermal, chemical, and mechanical properties of polyester fibers with a spunbonded structure to provide a substrate portion which is suitable for use as the absorbent core 24 of a dressing or of a diaper, for example. These properties include a relatively high tensile strength and elongation, and excellent tear strength.

In order to render the absorbent member 35 swellable upon contact with moisture, the substrate portion 37 is impregnated with a suitable water swellable material which herein is referred to as a superabsorbent material.

Superabsorbents are hydrophilic materials which can absorb and retain water under pressure without dissolution in the fluid being absorbed. See J. C. Djock and R. E. Klern "Review of Synthetic and Starch-Graft Copolymer Superabsorbents" prepared for the Absorbent Products Conference held Nov. 16-17, 1983 in San Antonio, Tex. and incorporated by reference hereinto. Properties such as enzyme stability, biodegradability, absorbent capacity and rate of uptake are used to characterize a superabsorbent material. One of the early superabsorbents was a saponified starch graft polyacrylonitrile copolymer. See U.S. Pat. No. 3,425,971. The above-identified patent disclosed saponifying starch-graft polyacrylonitrile copolymers with aqueous bases.

The two major superabsorbents which are available today are cellulosic or starch-graft copolymers and synthetic superabsorbents. There are two major broad classes of synthetic superabsorbents. These are the polyelectrolytes and the nonelectrolytes. The polyelectrolytes are the most important and fall into four classes—polyacrylic acid superabsorbents, polymaleic anhydride-vinyl monomer superabsorbents, polyacrylonitrile-based superabsorbents and polyvinyl alcohol superabsorbents. Of these, the polyacrylic acid and polyacrylonitrile-based superabsorbents are most common. As with cellulosic-graft copolymer superabsorbents, the capacity of synthetic superabsorbents decreases with increasing salinity.

The polyacrylic acid class of superabsorbents includes both homopolymers and copolymers of acrylic acids and acrylate esters. The monomer units usually are polymerized to produce a water-soluble polymer which is then rendered insoluble by ionic and/or covalent cross-linking. Cross-linking of the polymer may be accomplished with a multivalent cation, radiation, or with a cross-linking agent. The absorbency of the product is determined by the number of ionizable groups, usually carboxylates, and the cross-linking density.

The cross-linking density affects not only the absorbency, but also the time required to absorb and the strength of the gel formed. Generally, the higher the cross-linking density, the stronger is the gel which is formed. The time to reach absorbent capacity decreases as the cross-linking density increases, and the absorbent capacity decreases.

The spunbonded substrate portion 37 may be impregnated with any of several water blocking superabsorbent materials. In a preferred embodiment, it is impregnated with a superabsorbent material which is derived from an aqueous solution comprising acrylate polymeric material which combines acrylic acid and sodium acrylate functionalities and water.

The impregnating material of the preferred embodiment comprises a sodium salt of polyacrylic acid in which all the carboxylic groups may or may not be reacted with sodium. In other words, it is saponified in whole or in part. The level of saponification which may fall within a relatively wide range depends on desired properties. After the substrate portion 37 has been impregnated, the superabsorbent material is dried to provide a film on the substrate portion. It is desirable to impregnate the absorbent member 35 with a film of the impregnating material instead of a powder. The impregnated absorbent member 35 has a density of about 1.1 to 1.8 ounces per square yard which includes the density of the untreated substrate portion 37 increased 10 to 80%, i.e. the add-on, by the treating material.

In another embodiment, a Reemay ® spunbonded polyester material is impregnated with an aqueous solution comprising acrylates and acrylamide polymer powders mixed with water. The material impregnated with such a composition has a density which may represent an increase as high as about 80% of the density of the untreated substrate portion 37. In each of the embodiments just described, the impregnating material is mixture of water and a superabsorbent material in which the mixture comprises about 4 to 25% solids when the impregnating material is an aqueous solution and applied.

In general, the substrate portion 37 may be impregnated with (1) a material comprising polyacrylic acid, or (2) a material comprising polyacrylamide or (3) blends of (1) and (2) or salts thereof or (4) copolymers of acrylic acid and acrylamides and salts thereof as well as other similar superabsorbents.

Advantageously, in response to contact with waste liquid, the superabsorbent material in the absorbent core 24 swells to block the flow of liquid including that in a perpendicular direction normal to the body surface. The superabsorbent material also forms a gel and changes the viscosity of the ingressed liquid at the point of contact with the superabsorbent material, making it more viscous and consequently developing more resistance to flow. As a result, the flow of waste liquid from a point of entry is readily absorbed into a gel consistency.

The substrate portion 37 of the absorbent member 35 also possesses specific properties such as porosity and thickness which enhance its use as a water blocking element. Of importance is the need for the substrate portion to be made of a material which has a relatively high porosity. It has been found that the liquid absorbing capability of the substrate portion 37 increases as the porosity of the substrate portion increases. Porosity may be measured by air permeability in units of cubic feet per minute at a specified water pressure. At 0.5 inch of water pressure, typical porosities are in the range of about 120 to 1000 $CFM/ft^2$.

The superabsorbent capability of a Reemay ® spunbonded polyester impregnated material is a surprising result. Inasmuch as the Reemay material has a relatively high porosity, it would be expected that liquids would penetrate it rather easily. In at least one catalog which discloses a superbonded polyester tape having a relatively high porosity, mention is made that the tape has a relatively low moisture pickup, presumably by surface tension. This seemingly would lead one away from its use as a waste liquid superabsorbent tape for use in dressings such as diapers.

Evidently, because it is so porous and hence substantially cellular in structure, the substrate portion 37 is capable of accepting a substantial quantity of the impregnating material. As a result, an entering body liquid contacts a substantial area of the impregnating material which is liquid absorbing. There is a surprisingly fast reaction between the liquid absorbing material and the body liquid causing the liquid absorbing material to swell and block off reentry of perpendicular movement of the body liquid into the liquid pervious layer 22.

The porosity of the treated substrate portion 37 decreases with increasing thickness for a given web structure. In a preferred embodiment, the Reemay ® material is style 2014 which at 0.5 inch of water has a porosity of 800 $CFM/ft^2$. Reemay material marketed under code designation 2014 has a density of 1.0 ounce per square yard, has a thickness of 0.008 inch and is formed of substantially straight polyethylene terephthalate fibers. Reemay material having a code designation of 2024 has a density of 2.1 ounces per square yard, has a thickness of 0.012 inch, has a porosity of 350 $CFM/ft^2$ at 0.5 inch $H_2O$ and also is formed of substantially straight polyethylene terephthalate fibers. Reemay material having a code designation of 2415 has a density of 1.15 ounces per square yard, has a thickness of 0.014 inch, has a porosity of 700 $CFM/ft^2$ at 0.5 inch $H_2O$ and is formed of crimped polyethylene terephthalate fibers.

Obviously, various other grades and thickness of Reemay spunbonded polyester material or other similar materials may be used. Material densities of up to about 2 ounces per square yard are practical values. Practical material thickness may range from 0.005 inch to 0.012 inch thick. These values by no means limit the invention but represent the presently preferred ranges.

Although the porosity of the substrate portion 37 is relatively high, that of the superbsorbent impregnated portion, if any, is relatively low. The porosity of the substrate portion 37 must be balanced against other properties. For example, because the portion is to be embodied in a dressing adjacent to a moving body, it is beneficial for the substrate portion to have a relatively high tensile strength. For a given material width, the tensile strength decreases as the thickness decreases. Although a larger thickness is desired insofar as tensile strength is concerned, a larger thickness may result in less porosity, at least for those portions which are available commercially. Therefore, these two properties must be balanced against each other to arrive at a final thickness. As mentioned hereinbefore, the style 2014 preferred Reemay ® material has a thickness of 0.008 inch which is suitable for use in the dressing of this invention. The layers in FIG. 2 can be of different increasing porosities to allow the liquid to flow to the bottom impervious layer, and away from the skin.

As should be apparent, the thickness of each element of the superabsorbent article must be considered. The thickness is established while being mindful of the properties of porosity and tensile strength. The substrate portion 37 must not be too thin, else the tensile strength is affected adversely, and if too thick, the porosity and overall size of the dressing are affected adversely.

The description hereinbefore included an absorbent core 24 which included three impregnated absorbent members 35-35. It should be understood that a plurality of absorbent members 35-35 in FIGS. 1 and 2 may be different porosities which decrease in porosity in a direction outwardly from the skin. In other words, the absorbent member 35 contiguous to the pervious layer 22 is the most porous and least absorbent. The absorbent member 35 farthest from the pervious layer 22 is the least porous and the most absorbent. This arrangement allows the waste liquid to flow away from the skin.

Also, it is within the scope of this invention to coat the inner surface of the outer layer 26 with a relatively thin film of a superabsorbent material. This provides enhanced suitability for the article. Further within the scope of this invention is a superabsorbent article in which each component layer comprises a biodegradable material.

It is to be understood that the above-described arrangements are simply illustrative of the invention. Other arrangements may be devised by those skilled in the art which will embody the principles of the invention and fall within the spirit and scope thereof.

I claim:

1. A superabsorbent article, which comprises:
   a liquid pervious layer which is adapted to be positioned in engagement with a body from which a liquid is excreted;
   a liquid impervious layer which is spaced from said liquid pervious layer; and
   a liquid absorbent layer which is disposed between said liquid pervious and impervious layers and which comprises:
      a preformed substrate portion which has a relatively high tensile strength and a relatively high porosity and a relatively small thickness, said substrate portion being a spunbonded non-woven polyester material which comprises continuous filament polyester fibers that are randomly arranged, highly dispersed and bonded at filament junctions; and
      a superabsorbent material which has been caused to impregnate the preformed substrate portion to fill substantially cells thereof such that said preformed substrate portion impregnated with said superabsorbent material has a relatively low porosity.

2. The article of claim 1 wherein said substrate portion has been impregnated with a superabsorbent material comprising a mixture which comprises water and a superabsorbent material in which the mixture comprises about 4 to 25% by weight of solids.

3. The article of claim 2 wherein said superabsorbent material comprises an acrylate polymer which includes acrylic acid and sodium acrylate.

4. The article of claim 3 wherein said impregnated liquid absorbent layer has a unit weight which is equal to about 1.1 to 1.8 ounces per square yard.

5. The article of claim 2 wherein said substrate portion has a density and the density of the impregnated substrate portion is to about 10 to 80% greater than the density of the substrate portion.

6. The article of claim 2 wherein said superabsorbent material includes acrylate acrylamide.

7. The article of claim 1 wherein the relatively high porosity of said substrate portion prior to the impregnation thereof is in the range of about 120 to 1000 $CFM/ft^2$ at 0.5 inch of water.

8. The article of claim 1 wherein said substrate portion has a thickness which does not exceed about 0.010 inch and a tensile strength which is at least about 5 lbs/inch of width.

9. The article of claim 8 wherein said substrate portion, prior to impregnation thereof has a porosity in the range of about 300 to 1000 $CFM/ft^2$ at 0.5 inch of water.

10. The article of claim 1 wherein said superabsorbent material is selected from the group consisting of (1) polyacrylic acid; (2) polyacrylamide; blends of (1) and (2); salts of (1) and (2); and copolymers of (1) and (2).

11. The article of claim 1 wherein a plurality of liquid absorbent layers are disposed between said liquid pervious layer and said liquid impervious layer.

12. The article of claim 1 wherein an outer surface of said liquid impervious layer is provided with a relatively thin film of a superabsorbent material.

13. A liquid blocking member, which comprises:
    a preformed substrate portion which has a relatively high tensile strength and a relatively high porosity and a relatively small thickness, said substrate portion being a spun bonded non-woven polyester material which comprises continuous filament polyester fibers that are randomly arranged, highly dispersed and bonded at filament junctions; and
    a superabsorbent material which has been caused to impregnate said preformed substrate portion to fill substantially cells thereof such that said preformed substrate portion impregnated with said superabsorbent material has a relatively low porosity.

14. The member of claim 13 wherein said substrate portion comprises a non-woven material.

* * * * *